(12) United States Patent
Hayasaka (10) Patent No.: US 6,689,061 B2
(45) Date of Patent: Feb. 10, 2004

(54) ULTRASONIC IMAGING APPARATUS

(75) Inventor: Kazuyoshi Hayasaka, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/155,546

(22) Filed: May 24, 2002

(65) Prior Publication Data

US 2002/0183619 A1 Dec. 5, 2002

(30) Foreign Application Priority Data

May 30, 2001 (JP) .................................... 2001-162590

(51) Int. Cl.[7] ................................................ A61B 8/00
(52) U.S. Cl. ...................................... 600/437; 600/443
(58) Field of Search ................................ 600/407, 437, 600/438, 440–449, 450–471; 367/7, 11, 130, 138, 73; 181/102, 108, 112; 73/620–633; 128/916, 920; 342/25, 179

(56) References Cited

U.S. PATENT DOCUMENTS

| 4,159,462 | A | * | 6/1979 | Rocha et al. .................. 367/97 |
|---|---|---|---|---|
| 5,462,058 | A | | 10/1995 | Yamada et al. |
| 5,471,878 | A | | 12/1995 | Chiao et al. |
| 5,570,691 | A | | 11/1996 | Wright et al. |
| 5,582,173 | A | | 12/1996 | Li |

* cited by examiner

*Primary Examiner*—Ali M. Imam
(74) *Attorney, Agent, or Firm*—Carl B. Horton, Esq.; Armstrong Teasdale LLP (57) ABSTRACT

In order to facilitate ultrasonic imaging in a proper condition, a correlation value is calculated between a new image frame and a previous image frame each time the new image frame is obtained; and the acoustic line density of a scan is increased/decreased, the dynamic range of echo reception is enlarged/reduced, and the frame averaging intensity of an image frame is raised/lowered in response to an increase/decrease of the correlation value.

9 Claims, 8 Drawing Sheets

ULTRASONIC IMAGING APPARATUS

CROSS REFERENCE TO RELATED APPLICATIONS

This application claims the benefit of Japanese Application No. 2001-162590 filed May 30, 2001.

BACKGROUND OF THE INVENTION

The present invention relates to an ultrasonic imaging method and apparatus, and more particularly to ultrasonic imaging method and apparatus for repeatedly scanning the interior of a subject by an ultrasonic beam sequentially for every acoustic line to receive an echo, and producing an image frame for each scan based on an echo received signal.

In ultrasonic imaging, the interior of a subject is repeatedly scanned by an ultrasonic beam sequentially for every acoustic line to receive an echo, and an image frame is produced for each scan based on an echo received signal.

The definition of an image varies with the acoustic line density of the scan. As the acoustic line density becomes dense, the definition is improved; and as the acoustic line density becomes coarse, the definition is reduced. The range of echo intensity representation varies with the dynamic range of the echo reception. As the dynamic range is enlarged, the range of representation is enlarged; and as the dynamic range is reduced, the range of representation is reduced. The SNR (signal-to-noise ratio) of an image varies with the frame averaging intensity. As the frame averaging intensity is raised, the SNR is improved; and as the frame averaging intensity is lowered, the SNR is reduced.

A user of the ultrasonic imaging apparatus conducts imaging after appropriately adjusting the acoustic line density, dynamic range, frame averaging etc. for each imaging purpose. However, since such adjustment largely depends upon the skill of individual users, not every user can conduct imaging in a proper condition.

SUMMARY OF THE INVENTION

It is therefore an object of the present invention to provide an ultrasonic imaging method and apparatus by which imaging in a proper condition is facilitated.

(1) The present invention, in accordance with one aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; increasing the acoustic line density of the scan in response to an increase of the correlation value; and decreasing the acoustic line density of the scan in response to a decrease of the correlation value.

(2) The present invention, in accordance with another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; and acoustic line density adjusting means for increasing the acoustic line density of the scan in response to an increase of the correlation value and decreasing the acoustic line density of the scan in response to a decrease of the correlation value.

In the invention of the aspects described in (1) and (2), a correlation value is calculated between a new image frame and a previous image frame each time the new image frame is obtained; and the acoustic line density of the scan is increased in response to an increase of the correlation value, and is decreased in response to a decrease of the correlation value.

The correlation value increases with a smaller difference between the two image frames, i.e., a smaller temporal change of the image. Therefore, by increasing the acoustic line density to improve the image definition, precise imaging can be achieved for a slow-moving subject.

On the other hand, the correlation value decreases with a larger difference between the two images frames, i.e., a larger temporal change of the image. Therefore, by decreasing the acoustic line density to increase the frame rate of the image, imaging with good temporal resolution can be achieved for a fast-moving subject.

(3) The present invention, in accordance with still another aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; enlarging the dynamic range of the echo reception in response to an increase of the correlation value; and reducing the dynamic range of the echo reception in response to a decrease of the correlation value.

(4) The present invention, in accordance with still another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; and dynamic range adjusting means for enlarging the dynamic range of the echo reception in response to an increase of the correlation value, and reducing the dynamic range of the echo reception in response to a decrease of the correlation value.

In the invention of the aspects described in (3) and (4), a correlation value is calculated between a new image frame and a previous image frame each time the new image frame is obtained; and the dynamic range of echo reception is enlarged in response to an increase of the correlation value, and is reduced in response to a decrease of the correlation value.

The correlation value increases with a smaller difference between the two image frames, i.e., a smaller temporal change of the image. Therefore, by enlarging the dynamic range to enlarge the range of echo intensity representation, precise imaging can be achieved for a slow-moving subject.

On the other hand, the correlation value decreases with a larger difference between the two images frames, i.e., a larger temporal change of the image. Therefore, by reducing the dynamic range to reduce the range of echo intensity representation, simplified imaging can be achieved for a fast-moving subject.

(5) The present invention, in accordance with still another aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; raising the frame averaging intensity of the image frame in response to an increase of the correlation value; and lowering the frame averaging intensity of the image frame in response to a decrease of the correlation value.

(6) The present invention, in accordance with still another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; and frame averaging adjusting means for raising the frame averaging intensity of the image frame in response to an increase of the correlation value, and lowering the frame averaging intensity of the image frame in response to a decrease of the correlation value.

In the invention of the aspects described in (5) and (6), a correlation value is calculated between a new image frame and a previous image frame each time the new image frame is obtained; and the frame averaging intensity of the image frame is raised in response to an increase of the correlation value, and is lowered in response to a decrease of the correlation value.

The correlation value increases with a smaller difference between the two image frames, i.e., a smaller temporal change of the image. Therefore, by raising the frame averaging intensity to improve the SNR of the image, precise imaging can be achieved for a slow-moving subject.

On the other hand, the correlation value decreases with a larger difference between the two images frames, i.e., a larger temporal change of the image. Therefore, by lowering the frame averaging intensity to improve the responsiveness to a change, imaging with good temporal resolution can be achieved for a fast-moving subject.

(7) The present invention, in accordance with still another aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; increasing the acoustic line density of the scan in response to an increase of the correlation value; decreasing the acoustic line density of the scan in response to a decrease of the correlation value; enlarging the dynamic range of the echo reception in response to an increase of the correlation value; and reducing the dynamic range of the echo reception in response to a decrease of the correlation value.

(8) The present invention, in accordance with still another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; acoustic line density adjusting means for increasing the acoustic line density of the scan in response to an increase of the correlation value, and decreasing the acoustic line density of the scan in response to a decrease of the correlation value; and dynamic range adjusting means for enlarging the dynamic range of the echo reception in response to an increase of the correlation value, and reducing the dynamic range of the echo reception in response to a decrease of the correlation value.

In the invention of the aspects described in (7) and (8), a correlation value is calculated between a new image frame and a previous image frame each time the new image frame is obtained; and the acoustic line density of the scan is increased and the dynamic range of the echo reception is enlarged in response to an increase of the correlation value; and the acoustic line density is decreased and the dynamic range is reduced in response to a decrease of the correlation value.

Therefore, by increasing the acoustic line density to improve the image definition, and enlarging the dynamic range of the echo reception to enlarge the range of echo intensity representation, precise imaging can be achieved for a slow-moving subject.

Moreover, by decreasing the acoustic line density to increase the frame rate of the image, and reducing the dynamic range of the echo reception to reduce the range of echo intensity representation, simplified imaging with good temporal resolution can be achieved for a fast-moving subject.

(9) The present invention, in accordance with still another aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; increasing the acoustic line density of the scan in response to an increase of the correlation value; decreasing the acoustic line density of the scan in response to a decrease of the correlation value; raising the frame averaging intensity of the image frame in response to an increase of the correlation value; lowering the frame averaging intensity of the image frame in response to a decrease of the correlation value.

(10) The present invention, in accordance with still another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; acoustic line density adjusting means for increasing the acoustic line density of the scan in response to an increase of the correlation value, and decreasing the acoustic line density of the scan in response to a decrease of the correlation value; and frame averaging adjusting means for raising the frame averaging intensity of the image frame in response to an increase of the correlation value, and lowering the frame averaging intensity of the image frame in response to a decrease of the correlation value.

In the invention of the aspects described in (9) and (10), a correlation value is calculated between a new image frame and a previous image frame each time the new image frame is obtained; the acoustic line density of the scan is increased and the frame averaging intensity of the image frame is raised in response to an increase of the correlation value; and the acoustic line density is decreased and the frame averaging intensity is lowered in response to a decrease of the correlation value.

Therefore, by increasing the acoustic line density to improve the image definition, and raising the frame averaging intensity to improve the SNR of the image, precise imaging can be achieved for a slow-moving subject.

Moreover, by decreasing the acoustic line density to increase the frame rate of the image, and lowering the frame averaging intensity to improve the responsiveness to a change, imaging with good temporal resolution can be achieved for a fast-moving subject.

(11) The present invention, in accordance with still another aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; enlarging the dynamic range of the echo reception in response to an increase of the correlation value; reducing the dynamic range of the echo reception in response to a decrease of the correlation value; raising the frame averaging intensity of the image frame in response to an increase of the correlation value; and lowering the frame averaging intensity of the image frame in response to a decrease of the correlation value.

(12) The present invention, in accordance with still another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; dynamic range adjusting means for enlarging the dynamic range of the echo reception in response to an increase of the correlation value, and reducing the dynamic range of the echo reception in response to a decrease of the correlation value; and frame averaging adjusting means for raising the frame averaging intensity of the image frame in response to an increase of the correlation value, and lowering the frame averaging intensity of the image frame in response to a decrease of the correlation value.

In the invention of the aspects described in (11) and (12), a correlation value is calculated between a new image frame and a previous image frame each time the new image frame is obtained; dynamic range of echo reception is enlarged and the frame averaging intensity of the image frame is raised in response to an increase of the correlation value; and the dynamic range is reduced and the frame averaging intensity is lowered in response to a decrease of the correlation value.

Therefore, by enlarging the dynamic range to enlarge the range of echo intensity representation, and raising the frame averaging intensity to improve the SNR of the image, precise imaging can be achieved for a slow-moving subject.

Moreover, by reducing the dynamic range to reduce the range of echo intensity representation, and lowering the frame averaging intensity to improve the responsiveness to a change, simplified imaging with good temporal resolution can be achieved for fast-moving subject.

(13) The present invention, in accordance with still another aspect for solving the aforementioned problem, is an ultrasonic imaging method for repeatedly scanning the interior of a subject by an ultrasonic beam sequentially for every acoustic line to receive an echo, and producing an image frame for each scan based on an echo received signal, comprising the steps of: calculating a correlation value between a new image frame and a previous image frame each time the new image frame is obtained; increasing the acoustic line density of the scan in response to an increase of the correlation value; decreasing the acoustic line density of the scan in response to a decrease of the correlation value; enlarging the dynamic range of the echo reception in response to an increase of the correlation value; reducing the dynamic range of the echo reception in response to a decrease of the correlation value; raising the frame averaging intensity of the image frame in response to an increase of the correlation value; and lowering the frame averaging intensity of the image frame in response to a decrease of the correlation value.

(14) The present invention, in accordance with still another aspect for solving the aforementioned problem, is an ultrasonic imaging apparatus for repeatedly scanning the interior of a subject by an ultrasonic beam sequentially for every acoustic line to receive an echo, and producing an image frame for each scan based on an echo received signal, comprising: correlation value calculating means for calculating a correlation value between a new image frame and a previous image frame each time the new image frame is obtained; acoustic line density adjusting means for increasing the acoustic line density of the scan in response to an increase of the correlation value, and decreasing the acoustic line density of the scan in response to a decrease of the correlation value; dynamic range adjusting means for enlarging the dynamic range of the echo reception in response to an increase of the correlation value, and reducing the dynamic range of the echo reception in response to a decrease of the correlation value; and frame averaging adjusting means for raising the frame averaging intensity of the image frame in response to an increase of the correlation value, and lowering the frame averaging intensity of the image frame in response to a decrease of the correlation value.

In the invention of the aspects described in (13) and (14), a correlation value is calculated between a new image frame and a previous image frame each time the new image frame is obtained; the acoustic line density of the scan is increased, the dynamic range of the echo reception is enlarged, and the frame averaging intensity is raised in response to an increase of the correlation value; and the acoustic line density is decreased, the dynamic range is reduced, and the frame averaging intensity is lowered in response to a decrease of the correlation value.

Therefore, by increasing the acoustic line density to improve the image definition, enlarging the dynamic range to enlarge the range of echo intensity representation, and raising the frame averaging intensity to improve the SNR of the image, precise imaging can be achieved for a slow-moving subject.

Moreover, by decreasing the acoustic line density to increase the frame rate of the image, reducing the dynamic range to reduce the range of echo intensity representation, and lowering the frame averaging intensity to improve the responsiveness to a change, simplified imaging with good temporal resolution can be achieved for a fast-moving subject.

Preferably, the image frames for use in the calculation of the correlation value are those obtained by averaging a plurality of consecutive image frames, because the stability of the correlation value is improved.

As described above in detail, the present invention can provide an ultrasonic imaging method and apparatus by which imaging in a proper condition is facilitated.

Further objects and advantages of the present invention will be apparent from the following description of the preferred embodiments of the invention as illustrated in the accompanying drawings.

DETAILED DESCRIPTION OF THE INVENTION

Figure 1:
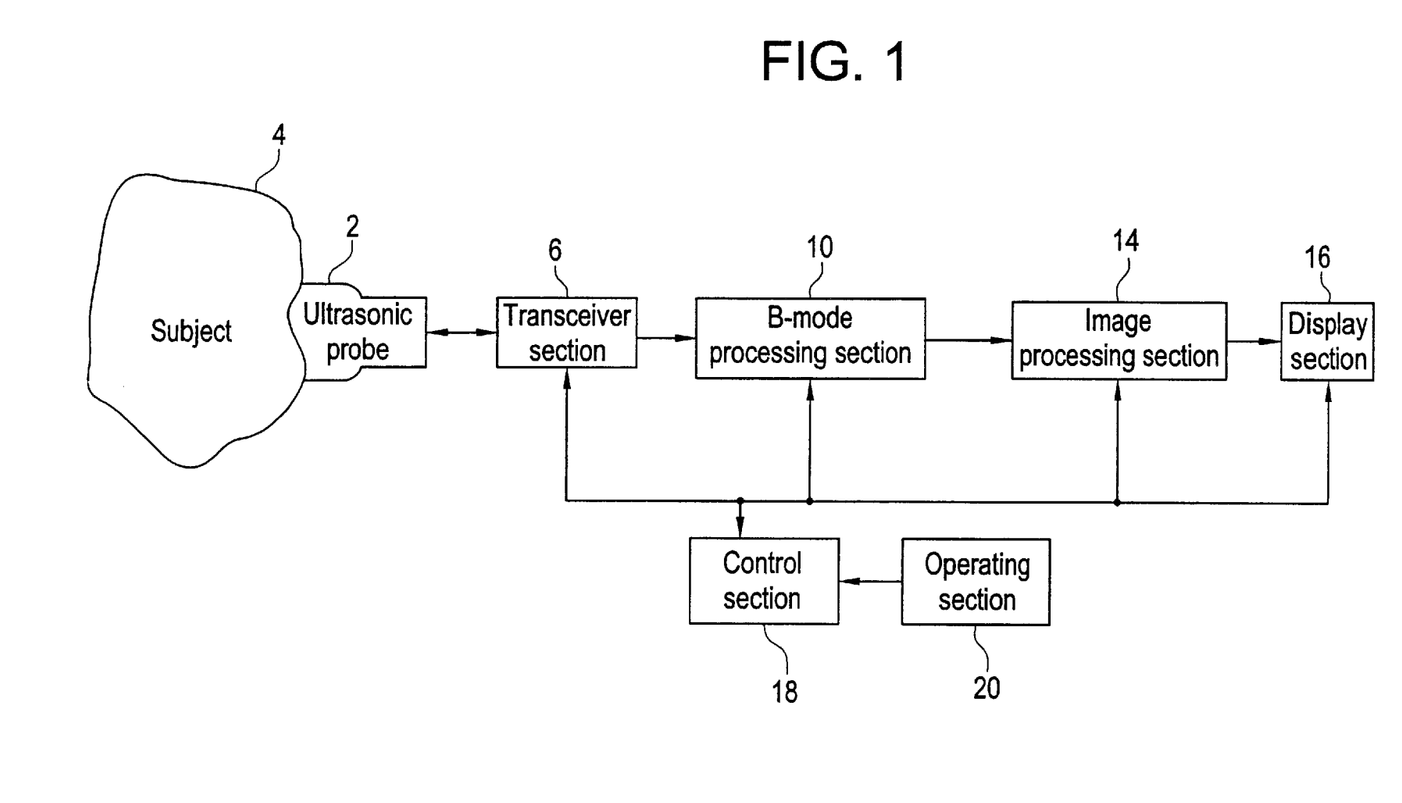
FIG. 1 is a block diagram of an apparatus in accordance with one embodiment of the present invention.

Several embodiments of the present invention will now be described in detail with reference to the accompanying drawings. It should be noted that the present invention is not limited to the embodiments. FIG. 1 shows a block diagram of an ultrasonic imaging apparatus, which is one embodiment of the present invention. The configuration of the apparatus represents an embodiment of the apparatus in accordance with the present invention. The operation of the apparatus represents an embodiment of the method in accordance with the present invention.

As shown in FIG. 1, the present apparatus has an ultrasonic probe 2. The ultrasonic probe 2 has an array of ultrasonic transducers (not shown). The individual ultrasonic transducers are made from a piezoelectric material such as PZT (lead zirconate titanate [Pb—Zr—Ti]) ceramic. The ultrasonic probe 2 is used abutted against a subject 4 by a user.

The ultrasonic probe 2 is connected to a transceiver section 6. The transceiver section 6 supplies driving signals to the ultrasonic probe 2 to transmit ultrasound. It also receives echo signals caught by the ultrasonic probe 2.

Figure 2:
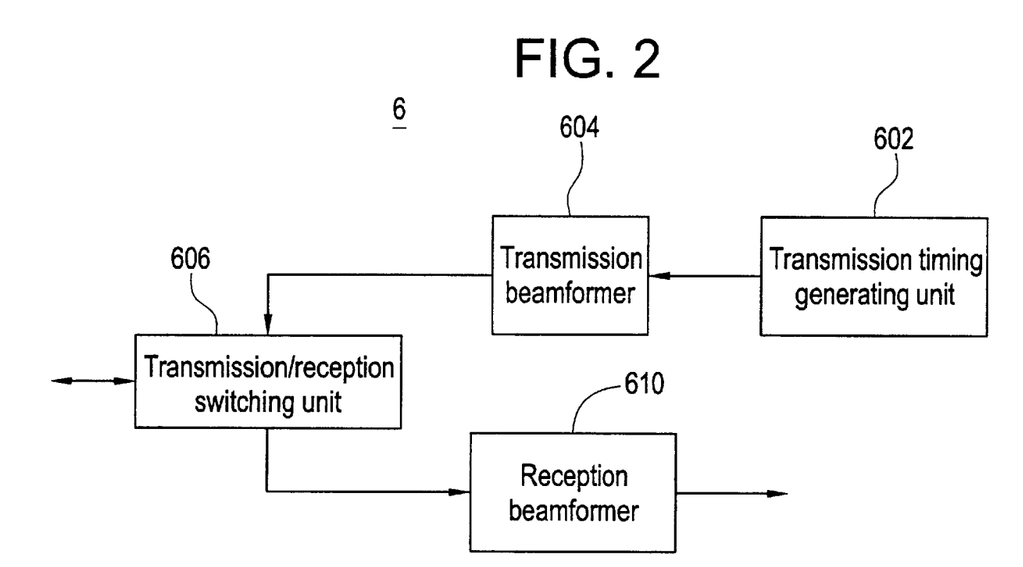
FIG. 2 is a block diagram of a transceiver section.

FIG. 2 shows a block diagram of the transceiver section 6. As shown, the transceiver section 6 has a transmission timing generating unit 602. The transmission timing generating unit 602 periodically generates a transmission timing signal, and inputs the signal to a transmission beamformer 604.

The transmission beamformer 604 is for performing beamforming for the transmission, involving generating a beamforming signal for forming an ultrasonic beam in a certain direction based on the transmission timing signal. The beamforming signal includes a plurality of driving signals that are given respective time differences corresponding to the direction. The beamforming is controlled by a control section 18, which will be described later. The transmission beamformer 604 inputs the transmission beamforming signal to a transmission/reception switching unit 606.

The transmission/reception switching unit 606 inputs the beamforming signal to the ultrasonic transducer array. A plurality of ultrasonic transducers that constitute a transmission aperture in the ultrasonic transducer array generate ultrasound having respective phase differences corresponding to the time differences in the driving signals. By wavefront synthesis of the ultrasound, an ultrasonic beam is formed along an acoustic line in a certain direction.

The transmission/reception switching unit 606 is connected with a reception beamformer 610. The transmission/reception switching unit 606 inputs the echo signals caught by a reception aperture in the ultrasonic transducer array to the reception beamformer 610. The reception beamformer 610 is for performing beamforming for the reception corresponding to an acoustic line for the transmission, involving imparting time differences to a plurality of received echoes to adjust their phases, and then adding the echoes to form an echo received signal along an acoustic line in a certain direction. The reception beamforming is controlled by the control section 18, which will be described later.

Figure 3:
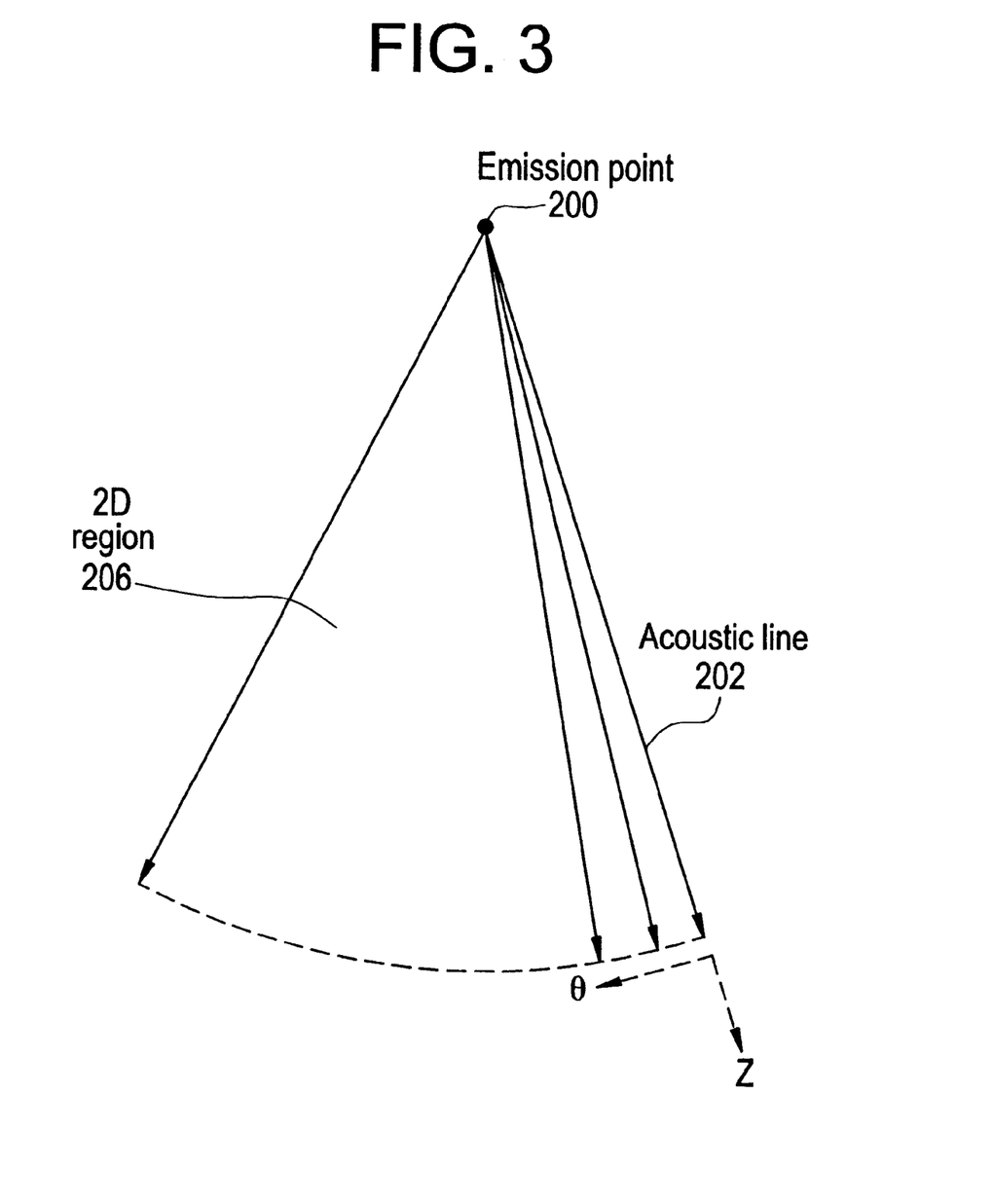
FIGS. 3–5 are schematic diagrams of acoustic line scanning.

The transmission of the ultrasonic beam is repeated at predefined time intervals according to the transmission timing signal generated by the transmission timing generating unit 602. Synchronously with the timing, the transmission beamformer 604 and the reception beamformer 610 change the direction of the acoustic line by a predefined amount. Thus, the interior of the subject 4 is sequentially scanned by the acoustic line. The transceiver section 6 having such a configuration performs a scan as exemplarily shown in FIG. 3. Specifically, a fan-shaped two-dimensional region 206 is scanned in the θ-direction by an acoustic line 202 extending from an emission point 200 in the z-direction, and a so-called sector scan is carried out.

Figure 4:
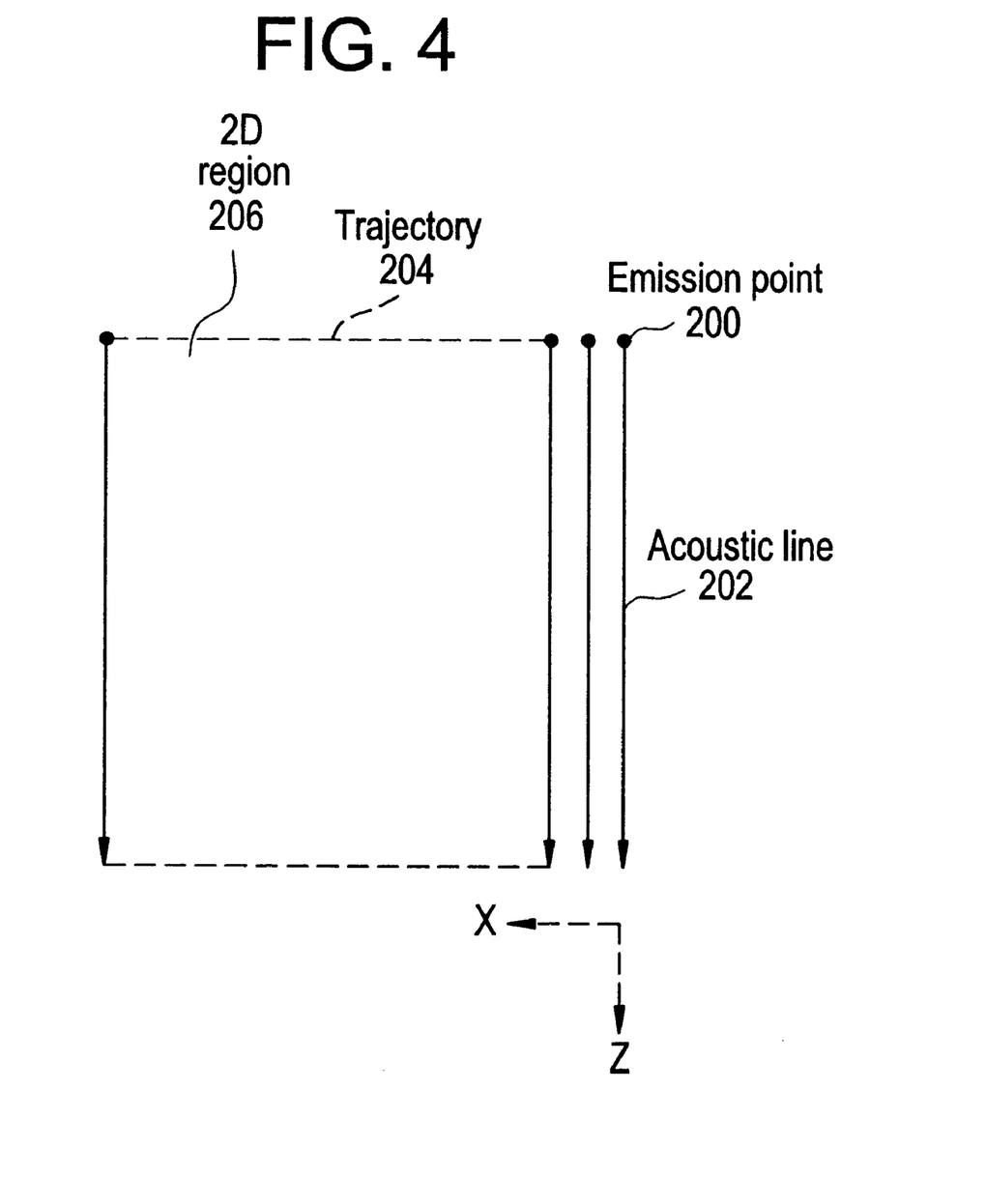

When the transmission and reception apertures are formed using part of the ultrasonic transducer array, a scan as exemplarily shown in FIG. 4 can be performed by sequentially shifting the apertures along the array. Specifically, a rectangular two-dimensional region 206 is scanned in the x-direction by translating an acoustic line 202, which emanates from an emission point 200 in the z-direction, along a linear trajectory 204, and a so-called linear scan is carried out.

Figure 5:
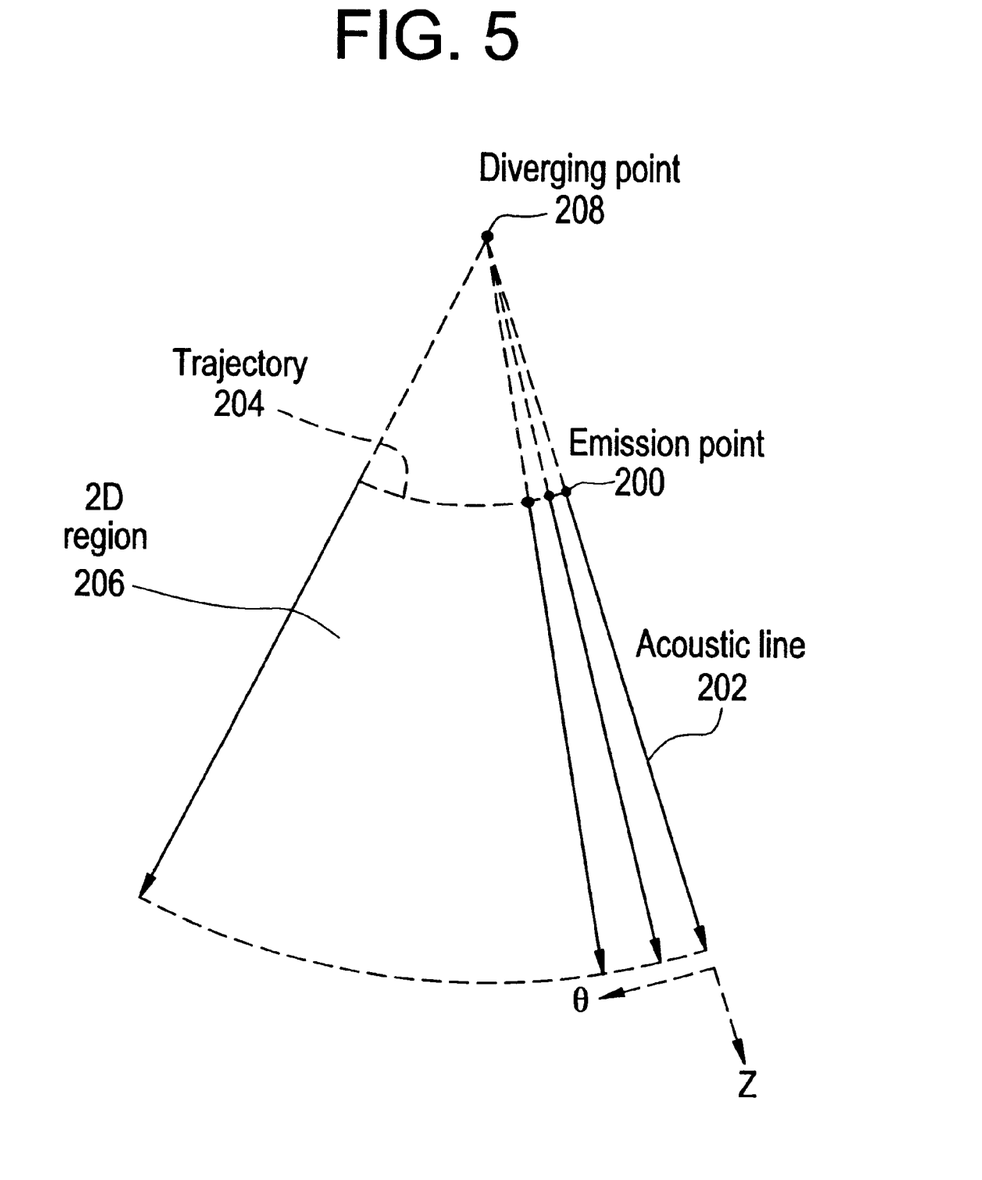

It will be easily recognized that when the ultrasonic transducer array is a so-called convex array, which is formed along an arc protruding in the direction of ultrasound transmission, a partial fan-shaped two-dimensional region 206 can be scanned in the θ-direction by performing an acoustic line scan similar to that for the linear scan and moving an emission point 200 of an acoustic line 202 along an arc-like trajectory 204, as exemplarily shown in FIG. 5, and a so-called convex scan is carried out.

Such scanning is repeated under control of the control section 18, which will be described later. The acoustic line density in scanning the two-dimensional region 206 is variable. The acoustic line density is changed by the transmission beamformer 604 and reception beamformer 610 under control of the control section 18. A portion including the control section 18, transmission beamformer 604 and reception beamformer 610 is an embodiment of the acoustic line density adjusting means in accordance with the present invention.

By changing the acoustic line density, the image definition is changed. Specifically, as the acoustic line density becomes dense, the image definition is improved; and as the acoustic line becomes coarse, the image definition is reduced. Moreover, by changing the acoustic line density, the frame rate is changed. The acoustic line density is inversely proportional to the frame rate. Thus, as the acoustic line density is increased, the frame rate is decreased, and as the acoustic line density is decreased, the frame rate is increased.

The transceiver section 6 is connected to a B-mode processing section 10. The echo received signal for each acoustic line output from the transceiver section 6 is input to the B-mode processing section 10.

Figure 6:
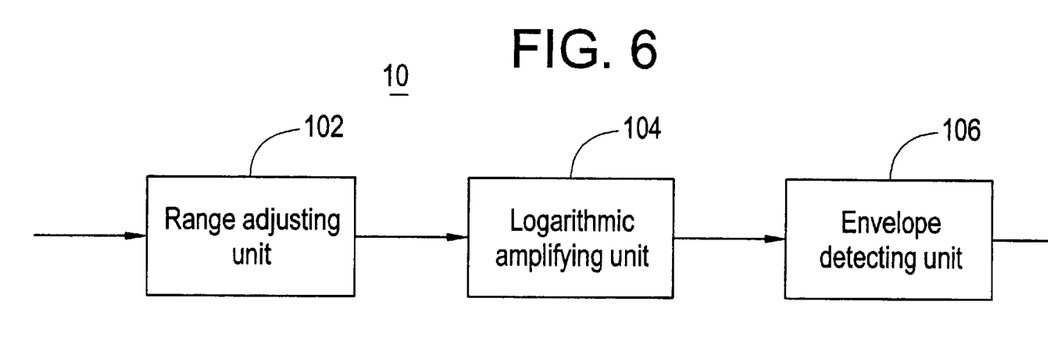
FIG. 6 is a block diagram of a B-mode processing section.

The B-mode processing section 10 is for generating B-mode image data. The B-mode processing section 10 comprises a range adjusting unit 102, a logarithmic amplifying unit 104 and an envelope detecting unit 106, as shown in FIG. 6.

The range adjusting unit 102 adjusts the dynamic range of the input signals under control of the control section 18, which will be described later. By enlarging the dynamic range, the range of echo intensity representation is enlarged; and by reducing the dynamic range, the range of representation is reduced. A portion including the control section 18 and the range adjusting unit 102 is an embodiment of the dynamic range adjusting means in accordance with the present invention.

The B-mode processing section 10 adjusts the input range of the echo received signal at the range adjusting unit 102; logarithmically amplifies the echo received signal at the logarithmic amplifying unit 104; detects its envelope at the envelope detecting unit 106 to obtain a signal indicating the intensity of the echo at each reflection point on an acoustic line, i.e., an A-scope signal; and generates B-mode image data using the amplitude of the A-scope signal at each instant as the brightness. The B-mode processing section 10 is connected to an image processing section 14. The image processing section 14 produces a B-mode image based on data supplied from the B-mode processing section 10.

Figure 7:
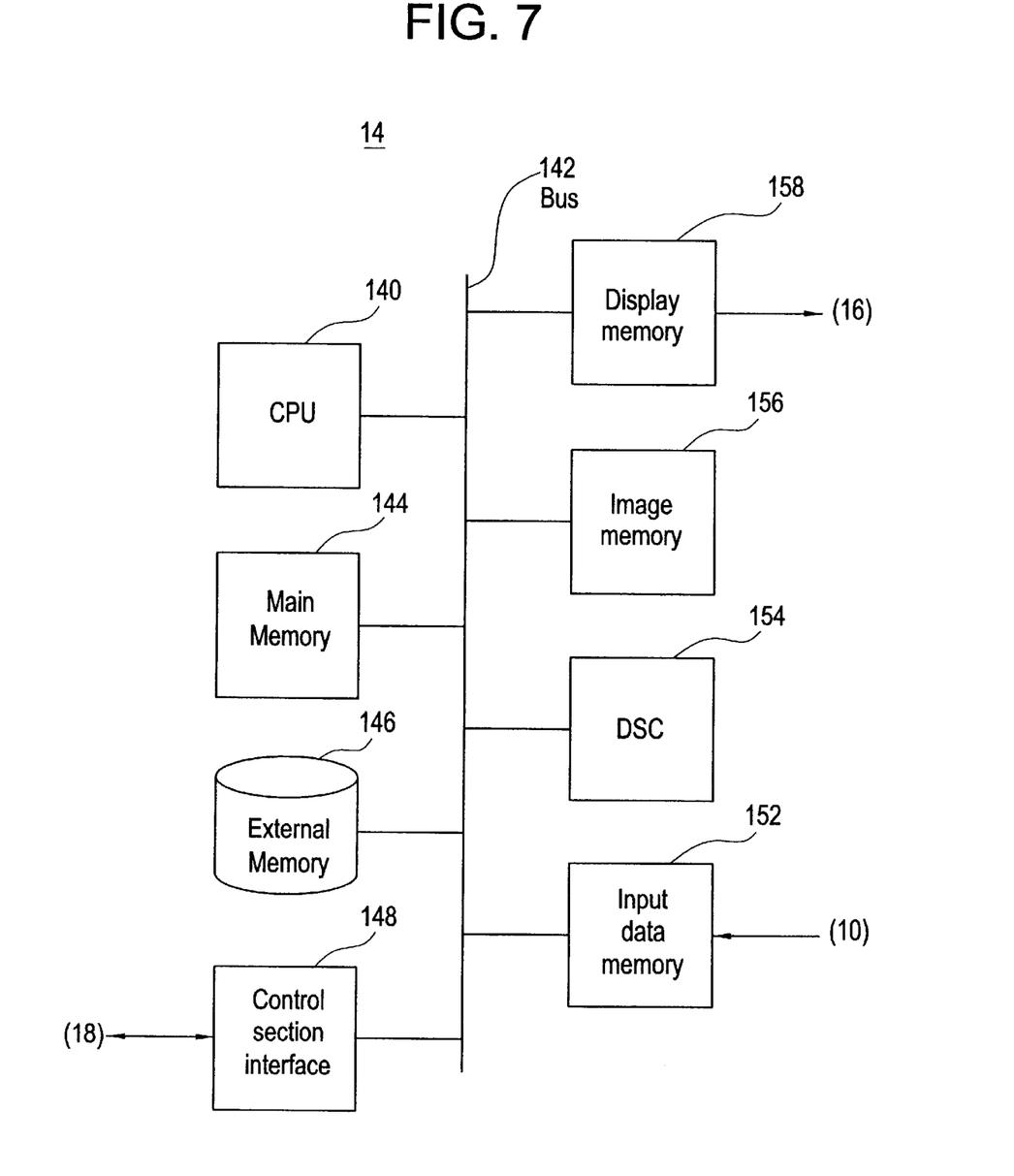
FIG. 7 is a block diagram of an image processing section.

The image processing section 14 has a central processing unit (CPU) 140, as shown in FIG. 7. The CPU 140 is connected via a bus 142 with a main memory 144, an external memory 146, a control interface 148, an input data memory 152, a digital scan converter (DSC) 154, an image memory 156, and a display memory 158.

The external memory 146 stores programs executed by the CPU 140. It also stores several kinds of data for use by the CPU 140 in executing the programs.

The CPU 140 carries out predefined image processing by loading a program from the external memory 146 into the main memory 144 for execution. The CPU 140 communicates control signals with the control section 18, which will be described later, via the control section interface 148 in the course of the program execution.

The B-mode image data for each acoustic line supplied from the B-mode processing section 10 is stored in the input data memory 152. The data in the input data memory 152 is scan-converted at the DSC 154 and written into the image memory 156 as an image frame.

CPU 140 performs frame averaging on the image frames in the image memory 156. The frame averaging refers to an operation that sets a pixel value in an image frame to an average value through a plurality of consecutive frames. As the number of image frames to be averaged is increased, the degree of averaging is raised and the SNR is improved. On the other hand, the number of image frames is decreased, the degree of averaging is lowered and the responsiveness to a temporal change of an image is improved. The degree of averaging is sometimes referred to as the frame averaging intensity herein.

The image frame after the frame averaging is written into the display memory 158. The image frame written into the display memory 158 is output to the display section 16, which will be described later.

The CPU 140 also calculates a two-dimensional cross-correlation between the latest image frame and an image frame obtained in a previous scan each time the latest image frame is written into the image memory 156. The CPU 140 is an embodiment of the correlation value calculating means in accordance with the present invention.

Moreover, the CPU 140 compares the resulting correlation value with the previous correlation value, and adjusts the frame averaging intensity in response to the result of the comparison relative to the previous correlation value. Specifically, when the correlation value increases, the frame averaging intensity is raised, and when the correlation value decreases, the frame averaging intensity is lowered. The CPU 140 is an embodiment of the frame averaging adjusting means in accordance with the present invention.

The correlation value increases as the difference of the images between the frames becomes smaller, and decreases as the difference becomes larger. The difference of the images between the frames is caused by motion of the image, and the motion of the image results from motion of the subject 4 or ultrasonic probe 2. Accordingly, the correlation value increases with smaller motion of the subject 4 or ultrasonic probe 2, and decreases with greater motion of the subject 4 or ultrasonic probe 2.

Therefore, when the correlation value increases, the frame averaging intensity is raised to improve the SNR for an image with smaller motion; and when the correlation value decreases, the frame averaging intensity is lowered to improve the responsiveness to a temporal change for an image with greater motion.

It should be noted that the latest image frame may be subjected to a certain degree of frame averaging before calculating the correlation value, and the correlation value may be calculated between such a frame-averaged image frame and the previous image frame subjected to the similar frame averaging. By such a process, the stability of the correlation value can be improved.

The image processing section 14 is connected with a display section 16. The display section 16 is supplied with an image signal from the image processing section 14, and displays an image based on the image signal. The display section 16 comprises a graphic display or the like employing a CRT (cathode ray tube) capable of displaying a color image.

The transceiver section 6, B-mode processing section 10, image processing section 14 and display section 16 are connected with the control section 18. The control section 18 supplies control signals to these sections for controlling their operation. The control section 18 is supplied with several kinds of signals from the controlled sections. The B-mode operation is executed under control of the control section 18.

The signals supplied from the image processing section 14 to the control section 18 include a signal indicative of an increase/decrease of the correlation value. The control section 18 controls the acoustic line density of the transmission beamformer 604 and reception beamformer 610 in the transceiver section 6 based on the signal indicative of an increase/decrease of the correlation value. Specifically, the acoustic line density is increased based on the signal indicative of an increase of the correlation value to improve the definition for an image with smaller motion. Similarly, the acoustic line density is decreased based on the signal indicative of a decrease of the correlation value to increase the frame rate for an image with greater motion.

The control section 18 also controls the dynamic range of the range adjusting unit 102 in the B-mode processing section 10 based on the signal indicative of an increase/decrease of the correlation value. Specifically, the dynamic range is enlarged based on the signal indicative of an increase of the correlation value to enlarge the range of echo intensity representation for an image with smaller motion; and the dynamic range is reduced based on the signal indicative of a decrease of the correlation value to reduce the range of echo intensity representation for an image with greater motion.

Figure 8:
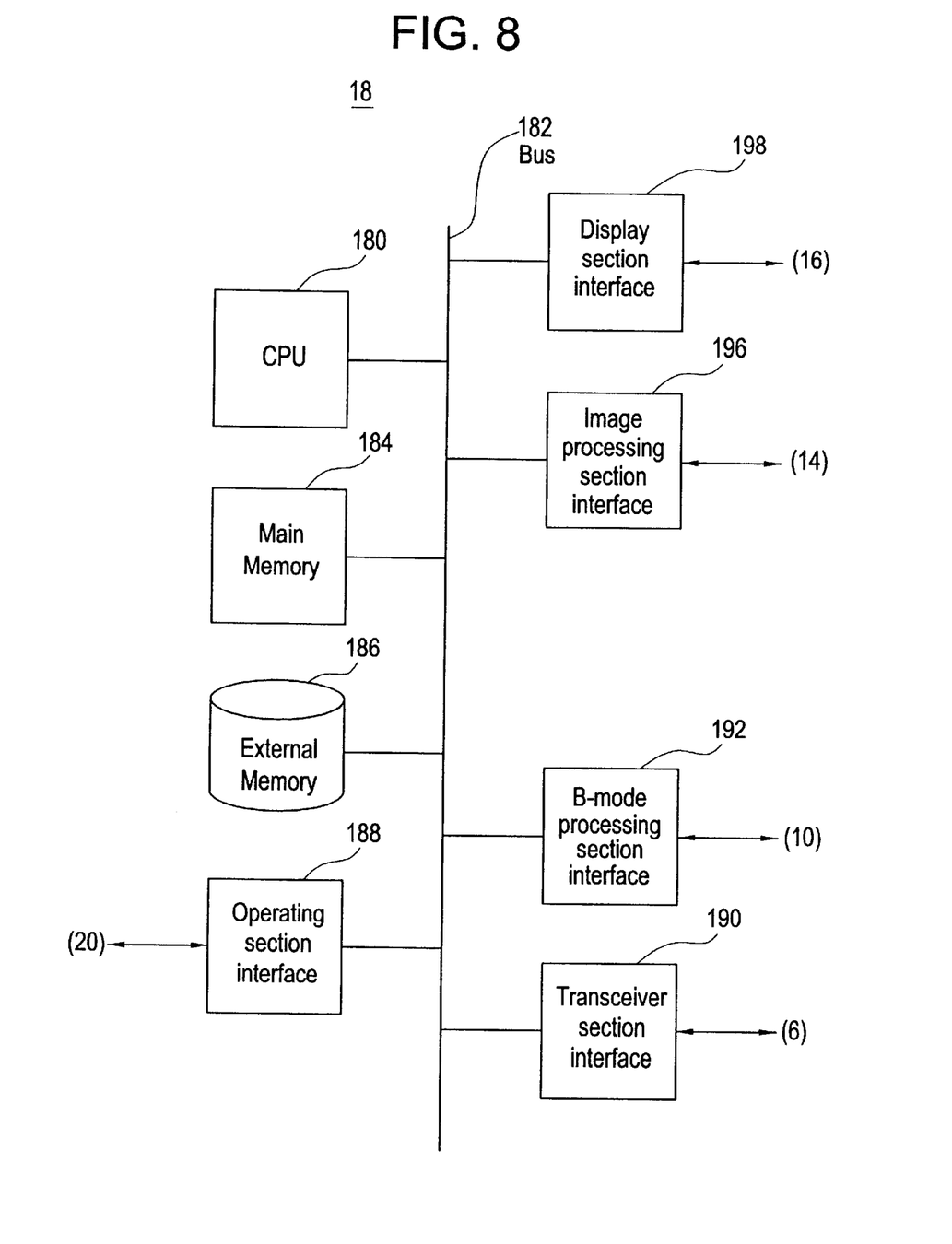
FIG. 8 is a block diagram of a control section.

The control section 18 has a CPU 180, as shown in FIG. 8. The CPU 180 is connected via a bus 182 with a main memory 184, an external memory 186, an operating section interface 188, a transceiver section interface 190, a B-mode processing section interface 192, an image processing section interface 196 and a display section interface 198.

The external memory 186 stores programs executed by the CPU 180. It also stores several kinds of data for use by the CPU 180 in executing the programs.

The CPU 180 carries out predefined control by loading a program from the external memory 186 into the main memory 184 for execution. The CPU 180 communicates control signals with the several sections via the operating section interface 188—display section interface 198 in the course of the program execution.

The control section 18 is connected with an operating section 20. The operating section 20 is operated by the user, and the section 20 inputs appropriate instructions and information to the control section 18. The operating section 20 comprises, for example, a keyboard, pointing device and other operating devices.

Now the operation of the present apparatus will be described. The user abuts the ultrasonic probe 2 against a desired portion on the subject 4, and operates the operating section 20 to perform imaging. Thus, B-mode imaging is performed under control of the control section 18.

Figure 9:
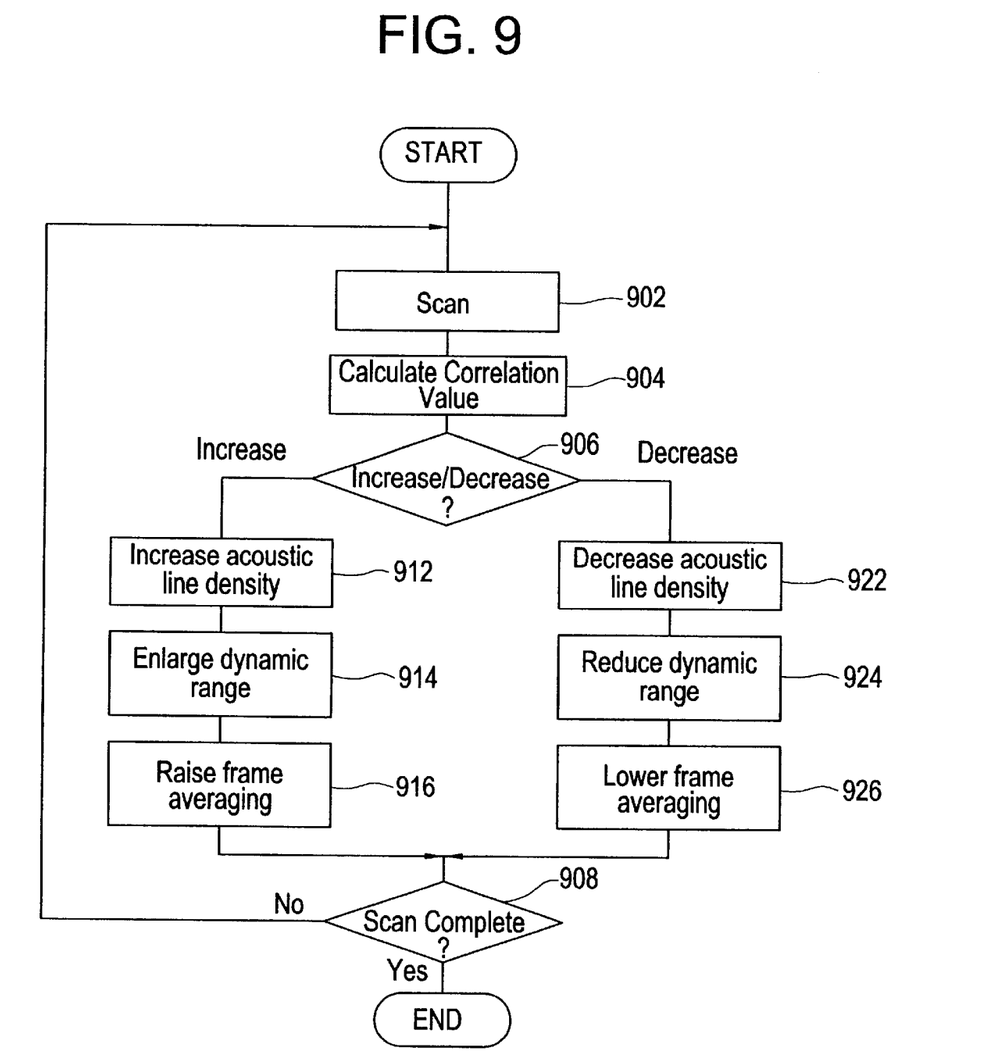
FIG. 9 is a flow chart of the operation of the apparatus in accordance with one embodiment of the present invention.

FIG. 9 shows a flow chart of the operation of the present apparatus. As shown, a scan is performed at Step 902. Specifically, the transceiver section 6 scans the interior of the subject 4 sequentially for every acoustic line and receives an echo each time through the ultrasonic probe 2. The acoustic line density of a scan at this time is set to a prespecified initial value or a default value.

The B-mode processing section 10 logarithmically amplifies the echo received signal supplied from the transceiver section 6 at the logarithmic amplifying unit 104 within the dynamic range of the range adjusting unit 102; envelope-detects the signal at the envelope detecting unit 106 to determine an A-scope signal; and generates B-mode image data for each acoustic line based on the A-scope signal. The dynamic range of the range adjusting unit 102 is set to a prespecified initial value or a default value at this time.

The image processing section 14 stores the B-mode image data for each acoustic line supplied from the B-mode processing section 10 in the input data memory 152. Thus, an acoustic line data space for the B-mode image data is formed in the input data memory 152.

The CPU 140 scan-converts the B-mode image data in the input data memory 152 at the DSC 154, and writes the Scan-converted data into the image memory 156. The CPU 140 also performs frame averaging on the image frames in the image memory 156, and writes the frame-averaged image frames into the display memory 158. The frame averaging intensity is set to a prespecified initial value or a default value at this time.

At Step 904, a correlation value calculation is performed on the image frames obtained by the repeated scans. The calculation of the correlation value is performed by the CPU 140 in the image processing section 140 in a manner as described earlier.

Next, at Step 906, an increase/decrease of the correlation value is checked. The check of the increase/decrease of the correlation value is performed by the CPU 140 in a manner as described earlier. However, the check is made relative to a prespecified initial value or a default value for the first time, and is made relative to the latest calculated correlation value for the second time or later.

When the correlation value increases, the acoustic line density is increased at Step 912, the dynamic range is enlarged at Step 914, and the frame averaging intensity is raised at Step 916.

The acoustic line density is increased by controlling the transceiver section 6 by the control section 18 in a manner as described earlier. The dynamic range is enlarged by controlling the B-mode processing section 10 by the control section 18 in a manner as described earlier. The frame averaging intensity is raised by the image processing section 14 in a manner as described earlier.

Thus, by increasing the acoustic line density to improve the image definition, enlarging the dynamic range to enlarge the range of echo intensity representation, and raising the frame averaging intensity to improve the SNR of the image, precise imaging can be achieved for an image with smaller motion.

It should be noted that any one or two of the increase of the acoustic line density, enlargement of the dynamic range and raising of the frame averaging may be performed rather than performing all of them.

When the correlation value decreases, the acoustic line density is decreased at Step 922, the dynamic range is reduced at Step 924, and the frame averaging intensity is lowered at Step 926.

Thus, by decreasing the acoustic line density to increase the frame rate of the image, reducing the dynamic range to reduce the range of echo intensity representation, and lowering the frame averaging intensity to improve the responsiveness to a change, simplified imaging with good temporal resolution can be achieved for a fast-moving subject.

It should be noted that any one or two of the decrease of the acoustic line density, reduction of the dynamic range and lowering of the frame averaging may be performed rather than performing all of them.

After such processing, a check is made as to whether the scan is completed at Step 908, and if not, the process goes back to Step 902. The same operation as above is repeated thereafter. Thus, imaging automatically adapted to a temporal change of an image can be performed.

While the present invention has been described with reference to preferred embodiments hereinabove, various changes or substitutions may be made on these embodiments by those ordinarily skilled in the art pertinent to the present invention without departing from the technical scope of the present invention. Therefore, the technical scope of the present invention encompasses not only those embodiments described above but all the embodiments that fall within the scope of the appended Many widely different embodiments of the invention may be constructed without departing from the spirit and the scope of the present invention. It should be understood that the present invention is not limited to the specific embodiments described in the specification, except as defined in the appended claims.

What is claimed is:

1. An ultrasonic imaging apparatus for repeatedly scanning the interior of a subject by an ultrasonic beam sequentially for every acoustic line to receive an echo, and producing an image frame for each scan based on an echo received signal, comprising:

a correlation value calculating device for calculating a correlation value between a new image frame and a previous image frame each time the new image frame is obtained; and an acoustic line density adjusting device for increasing the acoustic line density of said scan in response to an increase of said correlation value, and decreasing the acoustic line density of said scan in response to a decrease of said correlation value.

2. The ultrasonic imaging apparatus as defined in claim 1, wherein the previous and new image frames for use in the calculation of said correlation value are obtained by averaging a plurality of consecutive image frames.

3. The ultrasonic imaging apparatus as defined in claim 1, wherein each of the previous and the new image frame is obtained by scan-converting B-mode image data.

4. An ultrasonic imaging apparatus for repeatedly scanning the interior of a subject by an ultrasonic beam sequentially for every acoustic line to receive an echo, and producing an image frame for each scan based on an echo received signal, comprising:

a correlation value calculating device for calculating a correlation value between a new image frame and a previous image frame each time the new image frame is obtained; and a dynamic range adjusting device for enlarging the dynamic range of said echo reception in response to an increase of said correlation value, and reducing the dynamic range of said echo reception in response to a decrease of said correlation value.

5. The ultrasonic imaging apparatus as defined in claim 4, wherein the image frames for use in the calculation of said correlation value are those obtained by averaging a plurality of consecutive image frames.

6. The ultrasonic imaging apparatus as defined in claim 4, wherein each of the previous and the new image frame is obtained by scan-converting B-mode image data.

7. An ultrasonic imaging apparatus for repeatedly scanning the interior of a subject by an ultrasonic beam sequentially for every acoustic line to receive an echo, and producing a first image frame for each scan based on an echo received signal, comprising:

a correlation value calculating device for calculating a correlation value between a new image frame and a previous image frame each time the new image frame is obtained; and a frame averaging adjusting device for raising the frame averaging intensity of the first image frame in response to an increase of said correlation value, and lowering the frame averaging intensity of the first image frame in response to a decrease of said correlation value.

8. The ultrasonic imaging apparatus as defined in claim 7, wherein the image frames for use in the calculation of said correlation value are those obtained by averaging a plurality of consecutive image frames.

9. The ultrasonic imaging apparatus as defined in claim 7, wherein each of the previous and the new image frame is obtained by scan-converting B-mode image data.

* * * * *